United States Patent [19]

Ikegami et al.

[11] Patent Number: 4,978,775
[45] Date of Patent: Dec. 18, 1990

[54] PROCESS FOR PRODUCING BICYCLO[3.3.0]OCTANES

[75] Inventors: Shiro Ikegami; Yasuhiro Torizawa; Seizi Kurozumi, all of Tokyo, Japan

[73] Assignee: Teijin Limited, Osaka, Japan

[21] Appl. No.: 890,690

[22] PCT Filed: Nov. 14, 1985

[86] PCT No.: PCT/JP85/00636

§ 371 Date: Jul. 16, 1986

§ 102(e) Date: Jul. 16, 1986

[87] PCT Pub. No.: WO86/02923

PCT Pub. Date: May 22, 1986

[30] Foreign Application Priority Data

Nov. 16, 1984 [JP] Japan .................... 59-240592

[51] Int. Cl.$^5$ .................................. C07C 177/00
[52] U.S. Cl. ................................ 560/119; 562/501
[58] Field of Search .................... 560/119; 562/501

[56] References Cited

FOREIGN PATENT DOCUMENTS 79733 5/1983 European Pat. Off. ............ 560/120

OTHER PUBLICATIONS

Al-Kozimi, J. Am. Chem. Soc. 77, 2479 (1955).
Garmaise, J. Org. Chem. 27, 4509 (1962).
Robins, J.A.C.S. 103, 932 (1981).
Gemal, J.A.C.S. 103, 5454 (1981).
Gram, Organic Chemistry, p. 15 (1964)

Primary Examiner—Robert Gerstl
Attorney, Agent, or Firm—Sughrue, Mion, Zinn, Macpeak & Seas

[57] ABSTRACT

This invention provides a process for producing bicyclo[3.3.0]octanes expressed by the following formula [II]

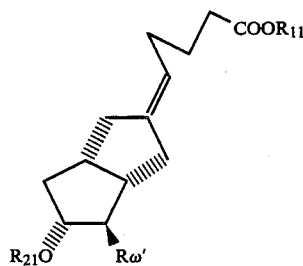

wherein $R_{11}$ represents H, a one-equivalent cation or $R_1$, $R_{\omega'}$, represents $R_{\omega'}$, and $R_{21}$ represents H or $R_2$, from a thiol compound expressed by the following formula [I],

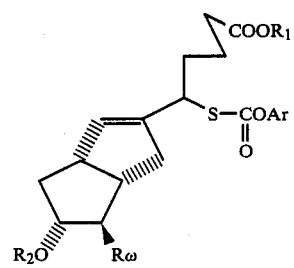

wherein $R_1$ represents a $C_{1-10}$ alkyl group, a substituted or unsubstituted phenyl group, a substituted or unsubstituted alicyclic group, a substituted or unsubstituted phenyl ($C_{1-2}$)alkyl group or a tri($C_{1-7}$hydrocarbyl)silyl group, Ar represents a substituted or unsubstituted aryl group, $R_\omega$ represents a substituted or unsubstituted $C_{1-13}$ alkyl group or a substituted or unsubstituted $C_{2-13}$ alkenyl group, and $R_2$ represents a hydroxyl-protecting group.

This process enables to obtain isocarbacyclines or synthetic intermediates therefor with industrial advantages.

9 Claims, No Drawings

PROCESS FOR PRODUCING BICYCLO[3.3.0]OCTANES

TECHNICAL FIELD

This invention relates to a process for producing bicyclo[3.3.0] octanes. More particularly, this invention relates to an industrially advantageous process for producing isocarbacyclins or their synthetical intermediates, bicyclo[3.3.0] octanes.

BACKGROUND OF THE ART

Carbocyclines are stable compounds of prostaglandin $I_2$ and are very useful compounds as an antithrombotic agent. It has recently been found that 9(0)-methano-$\Delta^6$-(9α)-prostaglandin $I_1$ (isocarbacyclin) is a compound which displays the strongest anticoagulant action against thrombocyte coagulation among the analogues of carbocycline and is expected to be used as medicine (Ikegami et al., Tetrahedron Lett., 33, 3493 (1983); ibid., 33, 3497, (1983); European Laid-Open Patent Publication No. 0134246).

With regard to the process for producing isocarbocycline, a method in which an epoxide compound expressed by a formula

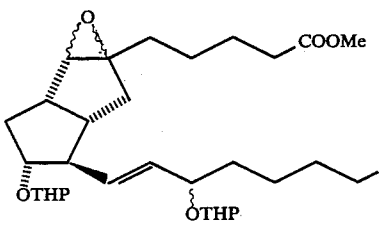

is used as an intermediate (Ikegami et al., Tetrahedron Lett., 33, 3493 (1983)) or a method in which an enolic compound expressed by a formula

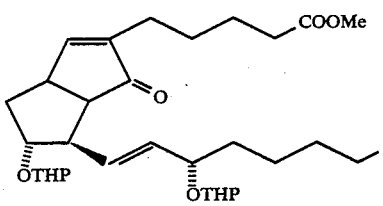

is used (Ikegami et al., Tetrahedron Lett., 33, 3497 (1983)) has hitherto been known. In these methods, however, the synthetic preparation of the intermediate epoxide compound or enolic compound from the starting material inevitably requires many processes and accordingly these methods of synthesizing isocarbacyclin can hardly be regarded as advantageous ones from the industrial viewpoint.

Apart from these methods, methods have recently been proposed to synthesize isocarbacyclin by use of a bicyclo[3.3.0] octane compound which is expressed by a formula shown below.

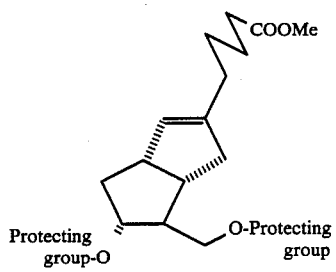

There are, for instance, such methods as (i) A method comprising introducing an α-chain to Corey lactone, a starting material, in the Wittig's reaction, establishing the aforementioned bicyclo[3.3.0] octane through an epoxide compound, and further subjecting to the oxidation reaction, Horner-Emmons reaction, and reduction reaction to give isocarbacyclin (Chemistry Letters, 1069 (1984));

(ii) A method comprising introducing two methylene groups to Corey lactone, a starting material, in the Wittig's reaction, establishing a diene compound via diol compound and aldehyde compound, which is then selectively reduced to give the aforementioned bicyclo[3.3.0] octane compound, and following the same procedures as taken in the preceding (i) to obtain isocarbacyclin (Chemistry Letters, 579 (1984)); and (iii) A method comprising introducing an α-chain to Corey lactone, a starting material, in the Wittig's reaction, establishing an aldehyde compound, which is then subjected to the intramolecular thermal reaction to establish the aforementioned bicyclo[3.3.0] octane compound, and subjecting this compound to the same procedure as taken in the abovementioned (i) to obtain isocarbacyclin (Tetrahedron Lett., 25, 1067 (1984)).

However, all of these methods have a demerit of being not industrially advantageous since they require multistage processes in obtaining the intermediate bicyclo[3.3.0] octane compound and the overall yield is not so large.

DISCLOSURE OF THE INVENTION

A primary object of this invention is to provide an industrially advantageous process for producing isocarbacyclins.

Another object of this invention is to provide an industrially excellent process for producing synthetic intermediates of isocarbacyclins.

A further object of this invention is to provide novel synthetic intermediates of isocarbacyclins.

Other objects of this invention will be clearly understood by referring to the following detailed description.

The objects and advantages of this invention will be achieved by the preparing process described below.

This is a process for preparing bicyclo[3.3.0] octanes expressed by the following formula (II)

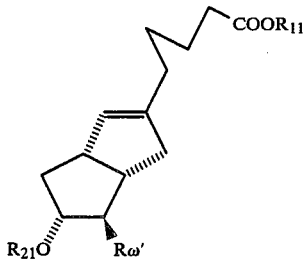

wherein $R_{11}$ indicates a hydrogen atom, $C_1 \sim C_{10}$ alkyl group, substituted or unsubstituted phenyl group, substituted or unsubstituted alicyclic group, substituted or unsubstituted phenyl ($C_1 \sim C_2$) alkyl group, tri ($C_1 \sim C_7$) hydrocarbon silyl group or one equivalent of cation; $R\omega'$ indicates a substituted or unsubstituted $C_1 \sim C_{13}$ alkyl group or substituted or unsubstituted $C_2 \sim C_{13}$ alkenyl group; and $R_{21}$ indicates a hydrogen atom or hydroxyl-protecting group;
which process comprises subjecting a thiol ester compound expressed by the following formula (I)

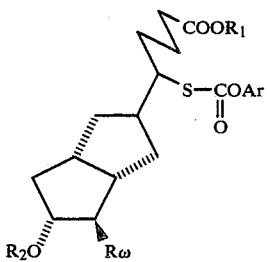

wherein $R_1$ indicates a $C_1 \sim C_{10}$ alkyl group, substituted or unsubstituted phenyl group, substituted or unsubstituted alicyclic group, substituted or unsubstituted phenyl ($C_1 \sim C_2$) alkyl group or tri ($C_1 \sim C_7$) hydrocarbon silyl group; Ar indicates a substituted or unsubstituted aryl group; $R\omega$ indicates a substituted or unsubstituted $C_1 \sim C_{13}$ C alkyl groups or a substituted or unsubstituted $C_2 \sim C_{13}$ alkenyl group; and $R_2$ indicates a hydroxyl-protecting group;
to the reduction reaction, followed by, if necessary, the deprotecting reaction, hydrolysis and/or salt-forming reaction.

$R_1$ in the aforementioned formula (I) indicates a $C_1 \sim C_{10}$ alkyl group, substituted or unsubstituted phenyl group, substituted or unsubstituted alicyclic group, substituted or unsubstituted phenyl ($C_1 \sim C_2$) alkyl group, or tri ($C_1 \sim C_7$) hydrocarbon silyl group.

As the $C_1 \sim C_{10}$ alkyl group, such linear or branched groups as methyl, ethyl, n-propyl, isopropyl, n-butyl, sec-butyl, tert-butyl, n-pentyl, n-hexyl, n-heptyl, n-octyl, n-nonyl, and n-decyl, for instance, may be mentioned.

As the unsubstituted phenyl substituent group, a halogen atom, hydroxyl group, $C_2 \sim C_7$ acyloxy group, $C_1 \sim C_4$ alkyl group which may be substituted by a halogen atom, $C_1 \sim C_4$ alkoxy group which may be substituted by a halogen atom, nitryl group, carboxyl group, and ($C_1 \sim C_6$) alkoxycarbonyl group are desirable ones.

As the halogen atom, fluorine, chlorine, and bromine are preferable, and fluorine and chlorine are especially preferable. As the $C_2 \sim C_7$ acyloxy group, acetoxy, propionyloxy, n-butyryloxy, iso-butyryloxy, n-valeryloxy, iso-valeryloxy, caproyloxy, enanthyloxy, and benzoyloxy may be mentioned. As the $C_1 \sim C_4$ alkyl group which may be substituted by a halogen atom, methyl, ethyl, n-propyl, iso-propyl, n-butyl, chloromethyl, dichloromethyl, and trifluoromethyl may be preferable. As the $C_1 \sim C_4$ alkoxy groups which may be substituted by a halogen atom, methoxy, ethoxy, n-propoxy, iso-propoxy, n-butoxy, chloromethoxy, dichloromethoxy, and trifluoromethoxy may be mentioned as preferable ones.

As the ($C_1 \sim C_6$) alkoxycarboxyl group, methoxycarbonyl, ethoxycarbonyl, butoxycarbonyl, and hexyloxycarbonyl may be mentioned.

The substituted phenyl group may have 1 to 3 substituents as mentioned above, preferably one substituent.

As the substituted or unsubstituted alicyclic group, a $C_3 \sim C_{10}$ cycloalkyl group, which is substituted by such substituents as mentioned above or unsubstituted, and cyclopropyl, cyclopentyl, cyclohexyl, and cycloheptyl, for instance may be mentioned, and cyclopentyl and cyclohexyl are preferable.

As the substituted or unsubstituted phenyl ($C_1 \sim C_2$) alkyl group, benzyl, α-phenetyl, and β-phenetyl whose phenyl group is substituted by the same substituent as mentioned above or not substituted, may be mentioned.

As the tri ($C_1 \sim C_7$) hydrocarbon silyl group, such tri ($C_1 \sim C_4$) alkylsilyl as trimethylsilyl, triethylsilyl, and t-butyldimethylsilyl groups; such diphenyl ($C_1 \sim C_4$) alkylsilyl as a t-butyldiphenylsilyl group; and tribenzylsilyl group may be mentioned as preferable ones.

Ar in the aforementioned formula (I) indicates a substituted or unsubstituted aryl group. As the substituted or unsubstituted aryl group like this, phenyl and naphthyl, which may be substituted by the same substituent as mentioned above or unsubstituted, may be mentioned.

$R\omega$ in the aforementioned formula (I) indicates a substituted or unsubstituted $C_1 \sim C_{13}$ alkyl group, or a substituted or unsubstituted $C_1 \sim C_{13}$ alkenyl group.

As the unsubstituted $C_1 \sim C_{13}$ alkyl group, such linear or branched alkyl groups as methyl, ethyl, n-propyl, iso-propyl, n-butyl, sec-butyl, tert-butyl, n-pentyl, n-hexyl, n-heptyl, n-octyl, n-nonyl, and n-decyl may be mentioned.

As the $C_2 \sim C_{13}$ alkenyl group, such linear or branched alkenyl groups as vinyl, 1-propenyl, 1-butenyl, 1-pentenyl, 1-hexenyl, 1-heptenyl, 1-octenyl, 1-nonenyl and 1-decenyl may be mentioned.

As the $C_1 \sim C_{13}$ alkyl group which has a substituent or the $C_2 \sim C_{13}$ alkenyl group which has a substituent, a hydroxyl group, protected hydroxyl group, vinyl group, $C_3 \sim C_7$ cycloalkyl group which may be substituted, $C_2 \sim C_4$ alkynyl group, $C_1 \sim C_4$ alkoxy group, phenyl group which may be substituted, and phenoxy group which may be substituted may be mentioned.

As the protected hydroxyl-protecting group, such tri ($C_1 \sim C_7$) hydrocarbon silyl groups as exemplified in defining $R_1$; groups which form an acetal bond with a hydrogen atom of such hydroxyl groups as methoxymethyl, 1-ethoxyethyl, 2-methoxy-2-propyl, 2-ethoxy-2-propyl, (2-methoxyethoxy) methyl, benzyloxymethyl, 2-tetrahydropyranyl, 2-tetrahydrofuranyl, and 6,6-dimethyl-3-oxa-2-oxobicyclo[3.3.0]hex-4-yl groups; and such $C_2 \sim C_7$ acyl groups as acetyl, propionyl n-butyryl, iso-butyryl, n-valeryl, iso-valeryl, caproyl, enanthyl, and benzoyl may be mentioned.

As the $C_3 \sim C_7$ cycloalkyl group, cyclopentyl and cyclohexyl, for instance, may be mentioned. These cycloalkyl groups may be substituted by the same substituent as the substituent of substituted phenyl group of $R_1$.

As the $C_2 \sim C_4$ alkoxy group, methoxy, ethoxy, propoxy, and butoxy, for instance, may be mentioned. As the substituent group of the phenyl group which may be substituted or the phenoxy group which may be substituted, a fluorine atom, methyl, trifluoromethyl, methoxy, and trifluoromethoxy, for instance, may be mentioned.

As $R\omega$ in the aforementioned formula (I), a substituted methyl group expressed by the following formula (IV)

(IV)

wherein $R_4$ indicates a hydroxyl-protecting group; or a substituted vinyl group expressed by the following formula (V)

(V)

wherein $R_1$ indicates a hydroxyl-protecting group; $R_6$ indicates a hydrogen atom, methyl group or vinyl group; $R_7$ indicates a substituted or unsubstituted $C_1 \sim C_9$ alkyl group, substituted or unsubstituted $C_2 \sim C_9$ alkenyl group, substituted or unsubstituted $C_2 \sim C_9$ alkynyl group, or substituted or unsubstituted $C_5 \sim C_6$ cycloalkyl group; and n indicates an integer 0 or 1, is preferable.

As the hydroxyl-protecting group indicated by $R_4$ in the aforementioned formula (IV) and by $R_5$ in the aforementioned formula (V), the same ones as those referred to in the above may again be mentioned. As the $C_1 \sim C_9$ alkyl group indicated by $R_7$ in the aforementioned formula (V), methyl, ethyl, n-propyl, n-butyl, n-pentyl, 1-methylpentyl, 2-methylpentyl, 1,1-dimethylpentyl, 1-methylhexyl, and 2-methylhexyl, for instance, may be mentioned. As the $C_2 \sim C_9$ alkenyl group, 2-pentenyl, 4-pentenyl, 2-methyl-3-pentenyl, hexenyl, 1,4-dimethyl-3-pentenyl, and 2,6-dimethyl-5-heptenyl may be mentioned. As the $C_2 \sim C_9$ alkynyl group, 2-butynyl, 2-pentynyl, 3-pentynyl, and 1-methyl-2-pentynyl may be mentioned. As the $C_5 \sim C_6$ cycloalkyl group, cyclopentyl and cyclohexyl, for instance, may be mentioned.

As the substituent groups of these $C_1 \sim C_9$ alkyl groups, $C_2 \sim C_9$ alkenyl groups, $C_2 \sim C_9$ alkynyl groups, and $C_5 \sim C_6$ cycloalkyl groups, the same substituent groups as the substituents of the $C_1 \sim C_{13}$ alkyl groups or those of the $C_2 \sim C_{13}$ alkenyl groups both indicated by the aforementioned $R\omega$ may be mentioned.

In the present invention, the thiol ester compound expressed by the aforementioned formula (I) is subjected to the reduction reaction to have the thiol ester group eliminated.

In the reduction reaction, it is desirable to use an organic tin compound expressed by the following formula (III)

(III)

wherein $R_3$ indicates a $C_1 \sim C_{10}$ alkyl group or a phenyl group

As the organic tin compound like this, trimethyltin hydride, triethyltin hydride, tri-n-butyltin hydride, tri-n-hexyltin hydride, tri-n-octyltin hydride, and triphenyltin hydride, for instance, may be mentioned. Of these, tri-n-butyltin hydride and triphenyltin hydride are preferable, and tri-n-butyltin hydride is especially preferable. It is advisable to use the organic tin compound in coexistence with a radical generating agent. As the radical generating agent, $\alpha,\alpha'$-azobisisobutyronitrile, bis-tert-butylperoxide, and tert-butylhydroperoxide are desirably used.

The organic tin compound is usually used in 2 to 20 molecular weight, preferably 2 to 5 molecular weight, against 1 molecular weight of the thiol ester compound of formula (I). The radical generating agent is usually used in 0.01 to 0.5 molecular weight, preferably 0.05 to 0.1 molecular weight, against 1 molecular weight of the thiol ester compound of formula (I).

It is desirable to carry out the reaction under an inert atmosphere such as nitrogen and argon, usually at 60° to 200° C., preferably at 100° to 150° C. The reaction may also be conducted in an inert organic medium. As the inert organic media, such aromatic hydrocarbons as benzene, toluene, and xylene and such aliphatic hydrocarbons as pentane and hexane may be mentioned and the aromatic hydrocarbons such as benzene and toluene are especially preferable.

The progress of reaction can be monitored observing the disappearance of the material by means of thin-layer chromatography and the reaction is usually completed in 1 to 5 hours. After the reaction is over, the reaction solution is freed of solvent, etc. by distillation. The resulting residue is refined by means of column chromatography on silica gel, etc. to give a compound resulting from the deprivation of the thiol ester group from the thiol ester compound of formula (I). Thus obtained compound may further be subjected to the deprotecting reaction, hydrolysis and/or salt-forming reaction, if necessary.

The deprotecting reaction is a publicly known reaction per se, and in case where the protecting group is a group which forms an acetal bond with a hydrogen atom of the hydroxyl group, the reaction is carried out by use of acetic acid, pyridinium salt of p-toluenesulfonic acid, or cation-exchange resin as a catalyst and by use of water, tetrahydrofuran, ethyl ether, dioxane, acetone, and acetonitrile as a reaction solvent. In case where the protecting group is a tri ($C_1 \sim C_7$) hydrocarbon silyl group, the deprotection is effected by use of acetic acid, tetrabutylammonium fluoride, and cesium, for instance. In case where the protecting group is an acyl group, the deprotection reaction may be carried out in an aqueous solution, or a water-alcohol mixed solution, of caustic soda, caustic potash, or calcium hydroxide; or a methanol or an ethanol solution containing sodium methoxide, potassium methoxide, or sodium ethoxide.

The hydrolytic reaction is a publicly known reaction per se and it can be carried out, for instance, by use of such an enzyme as lipase in water or in a water-containing solvent at a temperature ranging from $-10°$ C. to $+60°$ C. for 10 minutes to 24 hours.

The salt-forming reaction is a publicly known reaction per se and is carried out by allowing carboxylic acid, which is obtained in the aforementioned hydrolytic reaction, to be neutralized with an approximately equivalent weight of a basic compound of sodium hydroxide, potassium hydroxide, or sodium carbonate;

ammonia, trimethylamine, monoethanolamine, or morpholine according to an ordinary method.

In this way, bicyclo[3.3.0]octanes expressed by the following formula (II)

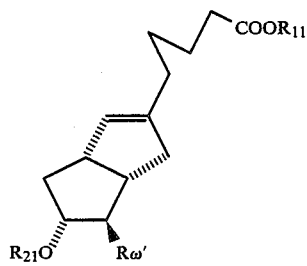
(II)

wherein $R_{11}$ indicates a hydrogen atom, ($C_1 \sim C_7$) alkyl group, substituted or unsubstituted phenyl group, substituted or unsubstituted alicyclic group, substituted or unsubstituted phenyl ($C_1 \sim C_2$) alkyl group, tri ($C_1 \sim C_7$) hydrocarbon silyl group or one equivalent of cation; $R\omega'$ indicates a substituted or unsubstituted $C_1 \sim C_{13}$ alkyl group or substituted or unsubstituted $C_1 \sim C_2$ alkenyl group; and $R_{21}$ indicates a hydrogen atom or hydroxyl-protecting group.

Thus obtained compounds are useful as isocarbacyclins which are medicines having a strong anticoagulant action against thrombocyte coagulation and are also useful compounds as the synthetic intermediates of such isocarbacyclins. For example, isocarbacyclins expressed by the following formula (II-1), which are obtained from a thiol ester compound in which $R\omega$ in the aforementioned formula (I) is a substituted vinyl group of formula (V),

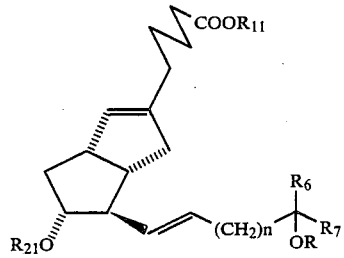
(II-1)

wherein $R_{11}$, $R_{21}$, $R_6$, $R_7$, and n are as defined hereinabove and $R_{51}$ indicates a hydrogen atom or a hydroxyl-protecting group.

are useful compounds as medicines. Also, bicyclo [3.3.0] octanes expressed by the following formula (II-2), which are obtained from a thiol ester compound in which $R\omega$ of the aforementioned formula (I) is a substituted methyl group of formula (IV),

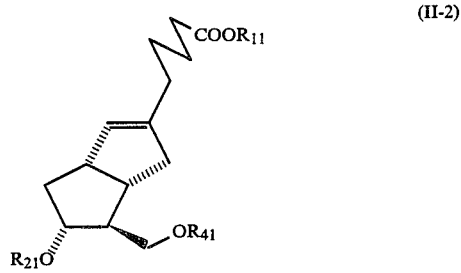
(II-2)

wherein $R_{11}$ and $R_{21}$ are as defined hereinabove and $R_{41}$ indicates a hydrogen atom or a hydroxyl-protecting group, can be led to isocarbacyclins by being subjected to the oxidative reaction to have a formyl group introduced at the 6-position, followed by the Horner-Emmons reaction with a phosphonate compound and the reduction reaction (Chemistry Letters, (1987)).

The thiol ester compound of formula (I), which is a starting material in the aforementioned producing process of the present invention, is a novel compound and can be produced according to the following method.

An enone compound expressed by the following formula (VI)

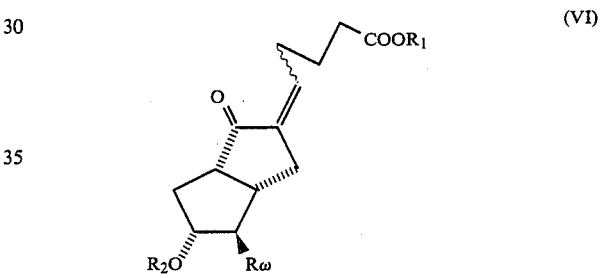
(VI)

wherein $R_1$, $R_2$, and $R\omega$ are as defined hereinabove, has its carbonyl group reduced to give an allyl alcohol compound expressed by the following formula (VII)

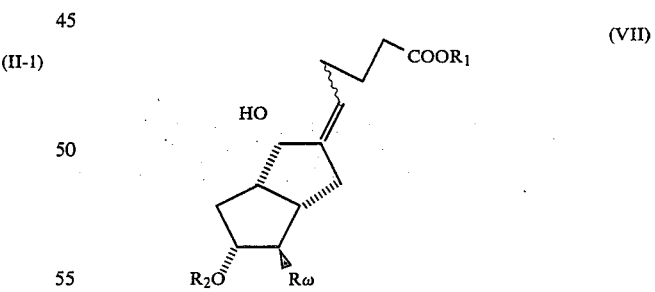
(VII)

wherein $R_1$, $R_2$, and $R\omega$ are as defined hereinabove, which is then made to react with an allylhalothionocarbonate compound expressed by the following formula (VIII)

(VIII)

wherein Ar is as defined hereinabove and X indicates a halogen group, to obtain a thiol ester compound of formula (I).

The enone compound of formula (VI) which is used in the above process ran be obtained by the following method.

Corey lactone expressed by the following formula (IX)

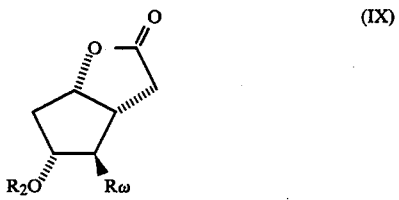

(IX)

wherein $R_2$ and $R\omega$ are as defined hereinabove, is reduced by lithium aluminum hydride. After the obtained diol modification is mesylated by use of methanesulfonyl chloride, it is treated with cesium acetate (Ikegami et al., Chem. Lett., 1555 (1984)), and the obtained diacetate modification is then hydrolyzed to give a diol compound expressed by the following formula (X)

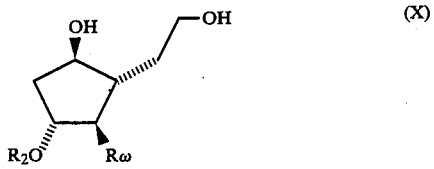

(X)

wherein $R_2$ and $R\omega$ are as defined hereinabove.
After this diol compound is methylsulfonated, it is made to react with the carbanion of methyl methylsulfinylmethyl sulfido (FAMSO), followed by the reduction to give a ketone compound expressed by the following formula (XI)

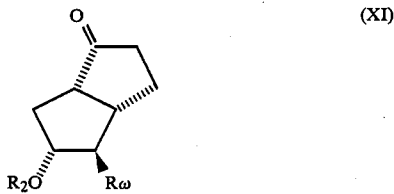

(XI)

wherein $R_2$ and $R\omega$ are as defined hereinabove, which compound is then allowed to undergo aldol condensation with an aldehyde compound expressed by the following formula (XII)

(XII)

wherein $R_1$ is as defined hereinabove, to give said starting material of the aforementioned formula (VI). The enone compound of formula (VI) can also be produced according to the method described in Japanese Patent Laid-Open Publication No. 34931/85.

The reduction of the carbonyl group of the enone compound of the aforementioned formula (VI) is a publicly known reaction per se and K-selectoride, L-selectoride, and sodium boron hydride-cerium thrichloride is especially preferable. The reaction conditions may be laid down according to the methods described in a document, J. Amer. Chem. Soc., 100, 2226 (1978). The allyl alcohol compound of the aforementioned formula (VII) can thus be obtained and then it is made to react with the allylhalothionocarbonate compound of the aforementioned formula (VIII). X in the formula (VIII) is a halogen atom, which includes chlorine and bromine and a chloride atom is especially preferable. In the reaction between the ally alcohol compound of formula (VII) and the allylhalothionocarbonate compound of formula VIII), 1.5 to 10 molecular weight, preferably 2 to 4 molecular weight, of allyhalothionocarbonate compound is used against 1 molecular weight of ally alcohol compound. The reaction is usually conducted in such a medium as methylene chloride, tetrahydrofuran, dimethoxyethane, ether, acetonitrile, pyridine, and hexamethylphosphorousamide (HMPA), of which methylene chloride and acetonitrile are used preferably. In order to make the reaction progress smoothly, it is a usual practice to use a base. As the base, there are such trialkylamines as trimethylamine, triethylamine, and diisopropylamine; such aromatic amines as pyridine, dimethylaminopyridine, and collidine; n-butyl lithium, and t-butoxy potassium, of which aromatic amines, inclusive of dimethylaminopyridine, and also n-butyl lithium are preferable, and the aromatic amines are especially preferable. It is desirable to use 1.5 to 10 molecular weight, preferably 2 to 6 molecular weight, of base against 1 molecular weight, of base against 1 molecular weight of the allyl alcohol compound.

The reaction temperature usually ranges from 0° to 50° C., preferably in the range of 1° to 20° C. and the conclusion of the reaction can be judged by the disappearance of the material observed by means of thin-layer chromatography. The reaction is usually completed in 2 to 24 hours at room temperature. After the reaction is over, the reaction solution is subjected to the ordinary treatments and the obtained crude product is purified by means of column chromatography on silica gel to give a thiol ester compound of formula (I).

As explained in detail hereinabove, the present invention provides a process in which the thiol ester compound of formula (I) is subjected to the reduction reaction to obtain bicyclo[3.3.0] octanes of formula (II) in high yields. Also, the thiol ester compound of formula (I) can be obtained advantageously on an industrial scale by allowing an allyl alcohol compound of formula (VII), which is easily obtained from Corey lactone of formula (IX), to react with an allylhalothionocarbonate compound of formula (VIII).

BEST MODE OF CARRYING OUT THE INVENTION

The following examples are given to furnish an explanation of the best mode of carrying out the present invention.

EXAMPLE 1

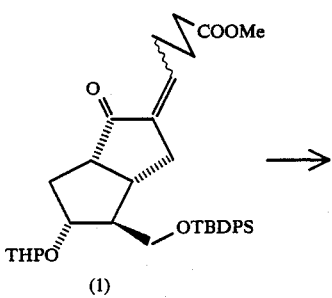

(1)

-continued

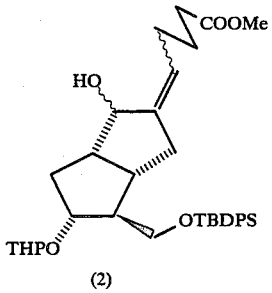

THP: Tetrahydropyranyl group
TBDPS: t-butyl diphenyl silyl group

Enone (1) (147 mg, 0.24 mmol) was dissolved in methanol (3 ml) and the solution was cooled to −40° C. CeCl$_3$.7H$_2$O (90.5 mg, 0.24 mmol, 1 equivalent) was first added to the solution and then NaBH$_4$ (11.0 mg, 0.29 mmol, 1.2 equivalents) was further added thereto little by little with stirring. After the reaction mixture was stirred under the same conditions for 5 minutes, the mixture was diluted with ether (20 ml). A saturated aqueous solution of NaCl (5 ml) and 10% HCl (one drop) were added thereto and the mixture was stirred for a while. The mixture was extracted with ether (50 ml) and the ether layer was washed with a saturated aqueous solution of NaHCO$_3$ (5 ml) and a saturated aqueous solution of NaCl (5 ml) and was dried over anhydrous Na$_2$SO$_4$. Upon removal of either by distillation under reduced pressure, crude allyl alcohol (2) (148 mg) was obtained in the form of a yellowish oily substance.

IR (liquid film): 3450, 2930, 2850, 1735, 1425, 1110, 700 cm$^{-1}$.

EXAMPLE 2

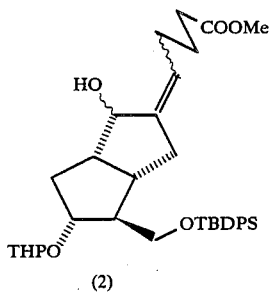

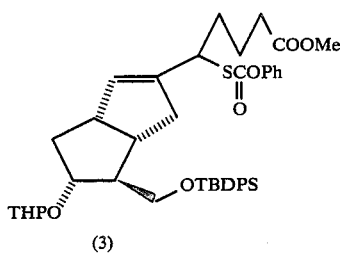

Allyl alcohol (2) (0.24 mmol), without having been purified, was dissolved in dried CH$_3$CN (4 ml). -dimethylaminopyridine (148 mg, 1.22 mmol, 5 equivalents) was added while cooling in an ice bath and further phenylchlormthionocarbonate (manufactured by Aldrich, 0.067 ml, 0.486 mmol, equivalents) was added thereto dropwise with a syringe. After the reaction mixture was stirred overnight at room temperature, the mixture was diluted with ether (20 ml) and saturated aqueous solution of NaCl (5 ml). The mixture was extracted with ether (50 ml) and the ether layer was washed with a saturated aqueous solution of NaCl (5 ml×2 times) and dried over Na$_2$SO$_4$ anhydride. After the removal of either by distillation, the obtained crude product was purified by column chromatography on silica gel (AcOEt: n-hexane=1:7) to give the desired thiol ester (3) (147.6 mg, yield from enone (1), 82%) in the form of a light yellow oily substance.

IR (liquid film) V max; 3010, 2910, 2825, 1715, 1580, 1460, 1415, 1090 cm.

1H-NMRδ (CDCl$_3$) ppm; 7.80~7.60 (m, 4H, aromatic), 7.50~7.60 (m, 11H, aromatic), 5.85, 5.65 (brs, 1H, olefinic), 3.6, 75 (s, 3H, OMe), 1.10 (s, 18H, t-Bu).

Mass (EI) m/e: 685 (M+-t-Bu), 601, 583.

EXAMPLE 3

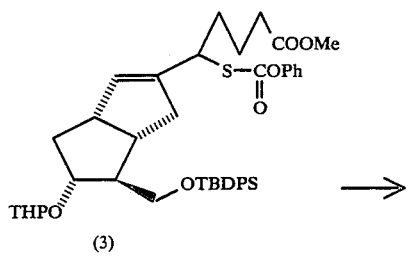

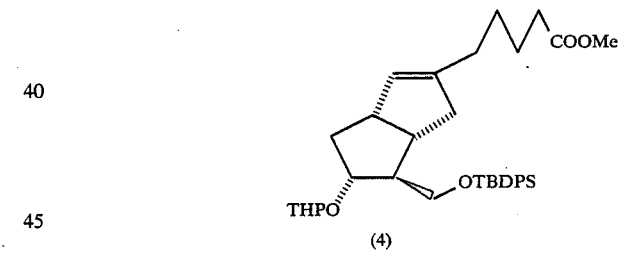

Thiol ester (3) (147 mg, 0.199 mmol) was dissolved in distilled benzene (5 ml) and tri-n-butyltin hydride (0.268 ml, 0.995 mmol, 5 equivalents) and a catalytically required amount of α,α'-azobisisobutyronitrile were added thereto. The mixture was refluxed with stirring for 3.5 hours while heating. After the reaction was completed, benzene was removed by distillation under reduced pressure and the resulting residue was separated and purified by column chromatography over silica gel (AcOEt: n-hexane=1:10) to obtain the desired olefin (4) (94 mg, yield 80%) in the form of a light yellow oily substance.

IR (liquid film) V max; 2925, 1735, 1420, 1110, 1070, 700 cm$^{-1}$.

1H-NMRδ (CDCl$_3$) ppm; 7.80~7.25 (m, 10H, aromatic), 5.30 (br.s, 1H, olefinic), 4.68~4.42 (m, 1H, OTHP), 3.60 (s, 3H, OMe), 1.00 (brs, 21H, CH$_3$). Massm/e; 533 (M+-t-Bu), 371

EXAMPLE 4~6

Allyl alcohols (5), (6), (7) were respectively treated according to the same method of preparation as Example 2 to obtain the products (8), (9), and (10). The reaction conditions and the spectrum data of the respective products are shown in Table 1.

TABLE 1

| Ally alcohol compound No. mg(mmol) | 4-Dimethyl-amino-pyridine mg(mmol) | Phenyl-chloro-thiono-carbonate mg(ml) (mmol) | Product thiol ester compound No. mg(mmol) | Yield % | Spectrum Data |
|---|---|---|---|---|---|
| (5) 120(0.20) | 120(1.0) | 81(0.065) (0.47) | (8) 110(0.15) | 74 | ms (m/e): 733, 687 ($M_+$-57) nmr (CDCl$_3$, δ): 0.8~0.95 (18H) 3.0~3.2 (1H), 3.68 (3H, s) 3.6~4.3 (3H, m) 5.55 (2H, m) 5.6~5.85 (1H, bs), 7.2~7.8 (5H) ir (liquid film cm$^{-1}$), 3020, 2920, 2830, 1720, 1580, 840, 780 |
| (6) 220(0.35) | 183(1.50) | 120(0.095) (0.70) | (9) 220(0.29) | 81 | ms (m/e): 722, 715 ($M^+$-57) nmr (CDCl$_3$, δ): 0.7~0.95 (24H), 3.0~3.2 (1H), 3.65 (3H, s), 3.6~4.3 (3H), 5.50 (2H, m), 5.5~5.8 (LH, bs), 7.2~7.8 (5H) ir (liquid film cm$^{-1}$): 3010, 1720, 835, 775 |
| (7) 150(0.25) | 159(1.30) | 86(0.070) (0.50) | (10) 155(0.21) | 84 | ms (m/e): 742, 686 ($M^+$-57) nmr (CDCl$_3$, δ): 0.7~0.9 (18H), 2.9~3.1 (1H) 3.65 (3H, s) 3.65~4.25 (3H, m), 5.50 (2H, m), 5.5~5.8 (1H, bs) 7.2~7.80 (5H), ir (liquid film cm$^{-1}$): 3020, 1720, 840, 775 |

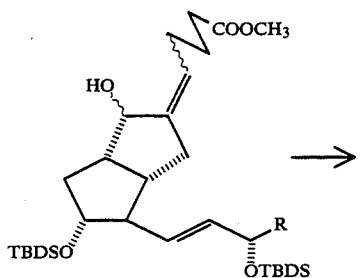

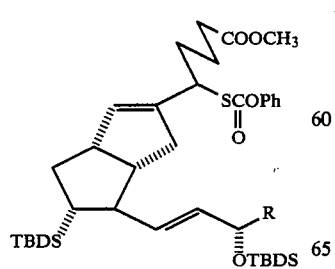

TBDS: t-butyldimethylsilyl group

EXAMPLES 7~9

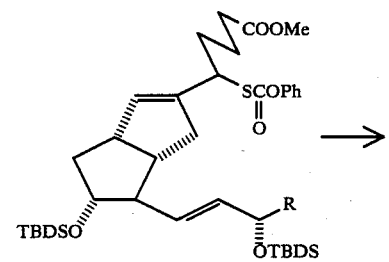

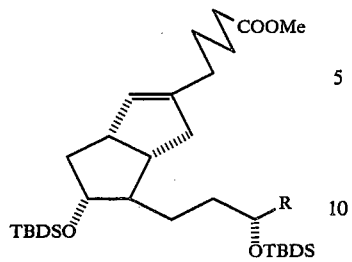

(8) R = pentyl
(9) R = 2-methylhexyl
(10) R = cyclopentyl
(11) R = pentyl
(12) R = 2-methylhexyl
(13) R = cyclopentyl Thiol esters (8), (9), and (10) were respectively treated according to the same method of preparation as Example 3 to obtain the corresponding products (11), (12), and (13). The reaction conditions and the spectrum data of the respective products are shown in Table 2.

TABLE 2

| Thiol ester (compound No.) mg(mmol) | Tributyl-tin-hydride mg(mmol) | Product thiol ester (compound No.) mg(mmol) | Yield (%) | Spectrum data |
|---|---|---|---|---|
| (8) 100(0.13) | 193(0.80) | (11) 71(0.12) | 92 | ms (m/e): 592, 535 ($M^+$ -57) nmr ($CDCl_3$, $\delta$): 0.75~0.95 (18H), 3.0 (1H, bs), 3.70 (3H, s), 3.6~4.1 (2H, m), 5.25 (1H, s), 5.50 (2H, m) ir (liquid film, $cm^{-1}$): 1740, 1260, 1110, 835, 775 |
| (9) 203(0.26) | 313(1.30) | 136(0.22) | 85 | ms (m/e): 620, 563 ($M^+$ -57) nmr ($CDCl_3$, $\delta$): 0.8~0.9 (24H), 2.6~3.2 (1H), 3.65 (3H, s), 3.5~4.3 (2H, m), 5.18 (1H, bs), 5.45 (2H, m) ir (liquid film, $cm^{-1}$): 1740, 1255, 1110, 1002, 968, 835, 770 |
| (10) 131(0.18) | 360(1.50) | (13) 88(0.15) | 83 | ms (m/e): 590, 533 ($M^+$ -57) nmr ($CDCl_3$, $\delta$): 0.8~0.9 (18H), 2.8~3.2 (1H), 3.70 (3H, s), 3.5~4.2 (2H, m), 5.20 (1H, bs), 5.50 (2H, m) ir (liquid film, $cm^{-1}$): 1745, 835, 775 |

Industrial Applications

The manufacturing process proposed by the present invention relates to an industrially excellent process for producing bicyclo[3.3.0] octanes and this invention has made it possible to obtain pharmaceutically useful iso-carbacyclins or their synthetic intermediates from the starting materials readily available on the market.

What we claim is:

1. A process for producing bicyclo[3.3.0] octanes expressed by the following formula (II)

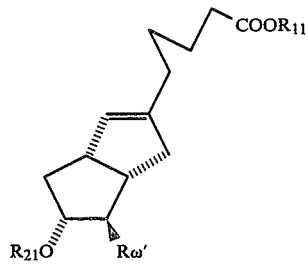

wherein $R_{11}$ indicates a hydrogen atom, $C_1 \sim C_{13}$ alkyl group, substituted or unsubstituted phenyl group, substituted or unsubstituted alicyclic group, substituted or unsubstituted phenyl ($C_1 \sim C_2$) alkyl group, tri ($C_1 \sim C_7$) hydrocarbon silyl group or one equivalent of cation; $R\omega$ indicates a substituted or unsubstituted $C_1 \sim C_{13}$ group or substituted or unsubstituted $C_2 \sim C_{13}$ alkenyl group; and $R_{21}$ indicates a hydrogen atom or hydroxyl-protecting group;

which process comprises subjecting a thiol ester compound expressed by the following formula (I)

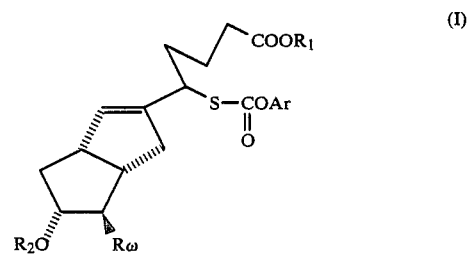

wherein $R_1$ indicates a $C_1 \sim C_{10}$ alkyl group, substituted or unsubstituted phenyl group, substituted or unsubstituted alicyclic group, substituted or unsubstituted phenyl ($C_1 \sim C_2$) alkyl group or tri ($C_1 \sim C_7$) hydrocarbon silyl group; Ar indicates a substituted or unsubstituted aryl group; $R\omega$ indicates a substituted or unsubstituted $C_1 \sim C_{13}$ group or a substituted or unsubstituted $C_2 \sim C_{13}$ alkenyl group; and $R_2$ indicates a hydroxyl-protecting group;

to a reduction reaction, followed by, if necessary, a deprotecting reaction, hydrolysis and/or salt-forming reaction.

2. The process for producing bicyclo[3.3.0] octanes according to claim 1, wherein said reduction reaction is carried out by use of an organic tin compound expressed by the following formula (III)

  (III)

wherein $R_1$ indicates a $C_1 \sim C_{10}$ alkyl group or phenyl group.

3. The process for producing bicyclo[3.3.0] octanes according to claim 1, wherein  $R\omega$ in the aforementioned formula (I) is a substituted methyl group expressed by the following formula (IV)

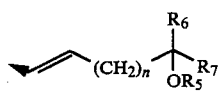  (IV)

wherein $R_4$ indicates a hydroxyl-protecting group.

4. The process for producing bicyclo[3.3.0] octanes according to claim 1, wherein $R\omega$ in the aforementioned formula (I) is a substituted vinyl group expressed by the following formula (V)

  (V)

wherein $R_5$ indicates a hydroxyl-protecting group; $R_6$ indicates a hydrogen atom, methyl group or vinyl group; $R_7$ indicates a substituted or unsubstituted $C_1 \sim C_9$ alkenyl group, substituted or unsubstituted $C_2 \sim C_9$ alkynyl group, or substituted or unsubstituted $C_{51} \sim C_6$ cycloalkyl group; and n indicates an integer 0 or 1.

5. A process for producing bicyclo[3.3.0] octanes expressed by the following formula (II)

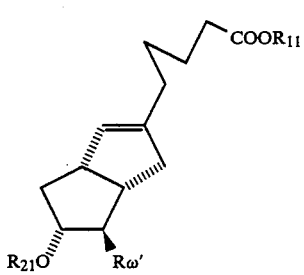  (II)

wherein $R_{11}$ indicates a hydrogen atom, $C_1 \sim C_{13}$ alkyl group, substituted or unsubstituted phenyl group, substituted or unsubstituted alicyclic group, substituted or unsubstituted phenyl ($C_1 \sim C_2$) alkyl group, tri ($C_1 \sim C_7$) hydrocarbon silyl group or one equivalent of cation; $R$, indicates a substituted or unsubstituted $C_1 \sim C_{13}$ alkyl group or substituted or unsubstituted $C_2 \sim C_{13}$ alkenyl group; and $R_{21}$ indicates a halogen atom or hydroxyl-protecting group;

which process comprises allowing an allyl alcohol compound expressed by the following formula (VII)

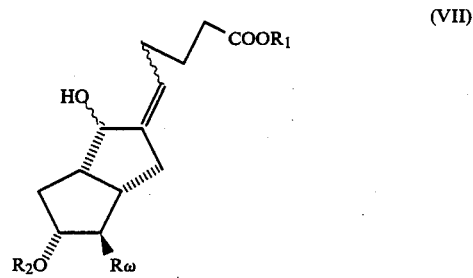  (VII)

wherein $R_1$ indicates a $C_1 \sim C_{10}$ alkyl group, substituted or unsubstituted phenyl group, substituted or unsubstituted alicyclic group, substituted or unsubstituted phenyl ($C_1 \sim C_2$) alkyl group or tri ($C_1 \sim C_7$) hydrocarbon silyl group; $R\omega$ indicates a substituted or unsubstituted $C_1 \sim C_{13}$ alkyl group or a substituted or unsubstituted $C_2 \sim C_{13}$ alkenyl group; and $R_2$ indicates a hydroxyl-protecting group;

to react with an allylhalothionocarbonate compound expressed by the following formula (VIII)

$$\underset{\underset{S}{\|}}{ArOCX} \quad (VIII)$$

wherein Ar indicates a substituted or unsubstituted aryl group; and X indicates a halogen atom, to obtain a thiol ester compound of formula (I)

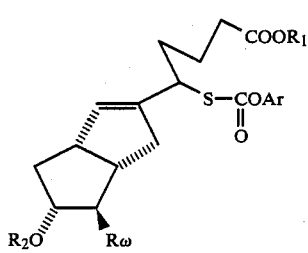  (I)

wherein $R_1$, $R_2$, Ar, and $R\omega$ are as defined hereinabove, which is then subjected to a reduction reaction, followed also by a deprotecting reaction, hydrolysis and/or salt-forming reaction, if necessary.

6. The process for producing bicyclo[3.3.0] octanes according to claim 5, wherein said allylhalothiono carbonate compound of the aforementioned formula (VIII) is subjected to the reaction with the allyl alcohol compound of the aforementioned formula (VII) in the presence of a base.

7. The process for producing bicyclo[3.3.0] octanes according to claim 6, wherein said base is an aromatic amine.

8. A process for producing bicyclo[3.3.0] octanes expressed by the following formula (II)

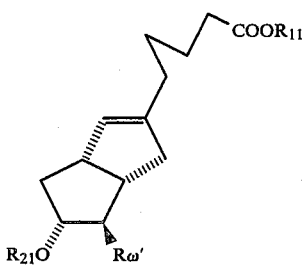

(II)

wherein $R_{11}$ indicates a hydrogen atom, $C_1 \sim C_{13}$ alkyl group, substituted or unsubstituted phenyl group, substituted or unsubstituted alicyclic group, substituted or unsubstituted phenyl ($C_1 \sim C_2$) alkyl group, tri ($C_1 \sim C_7$) hydrocarbon silyl group or one equivalent of cation; $R\omega'$ indicates a substituted or unsubstituted $C_1 \sim C_{13}$ alkyl group or substituted or unsubstituted $C_2 \sim C_{13}$ alkenyl group; and $R_{21}$ indicates a hydrogen atom or hydroxyl-protecting group;

wherein process comprises reducing an enone compound expressed by the following formula (VI)

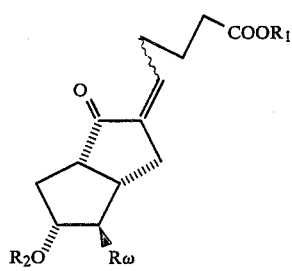

(VI)

wherein $R_1$ indicates a $C_1 \sim C_{10}$ alkyl group, substituted or unsubstituted phenyl group, substituted or unsubstituted alicyclic group, substituted or unsubstituted phenyl ($C_1 \sim C_2$) alkyl group or tri ($C_1 \sim C_7$) hydrocarbon alkyl group; $R\omega$ indicates a substituted or unsubstituted $C_1 \sim C_{13}$alkyl group or a substituted or unsubstituted $C_2 \sim C_{13}$ alkenyl group; and $R_2$ indicates a hydroxyl-protecting group;

to give an allyl alcohol compound expressed by the following formula (VII)

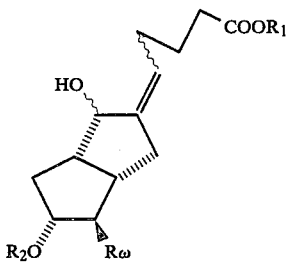

(VII)

wherein $R_1$, $R_2$, and $R\omega$ are as defined hereinabove, which is then made to react with an allylhalothionocarbonate compound expressed by the following formula (VIII)

(VIII)

wherein Ar indicates a substituted or unsubstituted aryl group; and X indicates a halogen atom;

to obtain a thiol ester compound expressed by the following formula (I)

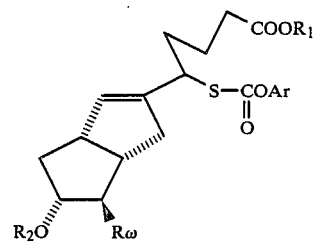

(I)

wherein $R_1$, $R_2$, Ar, and $R\omega$ are as defined hereinabove, and subjecting this compound to a reduction reaction followed by a deprotecting reaction, hydrolysis and/or salt-forming reaction, in necessary.

9. The process for producing bicyclo[3.3.0] octanes according to claim 8, wherein said reduction of an enon compound of the aforementioned formula (VI) is carried out by use of sodium boron hydride-cerium trichloride.

* * * * *